United States Patent [19]

Lombardi et al.

[11] Patent Number: 5,254,090
[45] Date of Patent: Oct. 19, 1993

[54] BALLOON CATHETER HAVING A DUAL LAYER INNER MEMBER

[75] Inventors: Edward J. Lombardi, Derry, N.H.; John M. Hegarty, Reading; Wayne P. Griffin, Dracut, both of Mass.

[73] Assignee: Kontron Instruments, Inc., Everett, Mass.

[21] Appl. No.: 928,136

[22] Filed: Aug. 11, 1992

Related U.S. Application Data

[63] Continuation of Ser. No. 640,951, Jan. 14, 1991, abandoned.

[51] Int. Cl.$^5$ .............................................. A61M 29/00
[52] U.S. Cl. .................................. 604/96; 606/192
[58] Field of Search .............. 604/96, 264, 280, 282; 606/192, 194; 138/137, 145, 146

[56] References Cited

U.S. PATENT DOCUMENTS

| | | | |
|---|---|---|---|
| 3,618,614 | 11/1971 | Flynn | 604/282 |
| 4,282,876 | 8/1981 | Flynn | 604/280 |
| 4,362,150 | 12/1982 | Lombardi et al. | 604/99 |
| 4,581,390 | 4/1986 | Flynn | 604/280 |
| 4,762,589 | 8/1988 | Akiyama et al. | 138/137 |
| 4,960,410 | 10/1990 | Pinchuk | 604/96 |
| 5,041,089 | 8/1991 | Mueller et al. | 604/280 |
| 5,052,444 | 10/1991 | Messerly et al. | 138/137 |
| 5,085,649 | 2/1992 | Flynn | 604/282 |

*Primary Examiner*—John D. Yasko
*Assistant Examiner*—Anthony Gutowski
*Attorney, Agent, or Firm*—Morgan & Finnegan

[57] ABSTRACT

A balloon catheter with an inner elongated member having an inner layer of a soft elastomeric polyurethane material and an outer layer of a hard plastic nylon material, which is formed by forming the outer layer onto the inner layer by coextrusion.

5 Claims, 2 Drawing Sheets

BALLOON CATHETER HAVING A DUAL LAYER INNER MEMBER

This is a continuation of co-pending application Ser. No. 07/640,951, filed on Jan. 14, 1991 (now abandoned).

BACKGROUND OF THE INVENTION

Intra-aortic balloon (hereinafter IAB) apparatus, more particularly percentaneous IAB apparatus are now widely used for intra-aortic balloon pumping in cardiogenic shock due to acute infraction, post-operative severe low cardiac output state, or inability to wean from cardiopulmonary bypass, refractory unstable angina in the period before and after infarction, recurrent life-threatening tachyarrhythmias, and preoperative support in the present of severe left ventricular dysfunction. Additionally, intra-aortic balloon pumping has been used both experimentally and clinically to reduce infarct size. Such devices have been disclosed in U.S. Pat. No. 4,362,150, the disclosure of which is incorporated, in toto, herein.

One method of inserting an IAB into a patient is via a non-surgical insertion of the device through the femoral artery of the patient. This is the so-called Seldinger technique.

After insertion of the balloon catheter into the patient's femoral artery, the device must be fed through the patient's arterial system until the IAB is correctly positioned for use, usually before the subclavian artery.

This insertion process can induce trauma to the walls of the patient's arterial or venous system. A problem attendant with the insertion procedure occurs in maneuvering the device along the arterial route which may require the twisting and turning of the device.

Trauma can be minimized by providing a flexible IAB which bends in conformance with the passageways. However, there must also be a balance of flexibility and rigidity so that some degree of directional control remains and to prevent or avoid kinking.

Although flexible IAB's have been commercially available for some time, there have been numerous occurrences of central lumen failures in IAB's. Prior art central lumen include a tube made from a single homogeneous plastic while other prior art IAB's have employed a central lumen having a metal coil embedded within the wall of a plastic tube of a single homogeneous plastic material.

These and similar problems have arisen with devices which are inserted into a patient's arterial or venous system and which need to be maneuvered through the system.

SUMMARY OF THE INVENTION

It is an object of the present invention to provide an improved catheter that is particularly well suited for insertion into a patient's arterial.

A further objective is to provide a durable and flexible catheter for use in an IAB or other apparatus in which a catheter is inserted into a patient's arterial system and guided therethrough.

A still further objective is to provide a catheter having a low kink radius and whose flexibility facilitates insertion of the catheter and the guiding of the catheter through tortuous arteries.

A yet further objection of the present invention is to provide a catheter which because of the low kink radius has especially good resiliency characteristics.

To achieve the foregoing and other objectives and in accordance with the purpose of the present invention, a catheter or central lumen is formed which is an elongated hollow member formed of an inner layer and an outer layer each said layer being composed of a different material and each material having its own unique chemical and physical properties. The inner layer is comprised of a soft elastomeric plastic material that imparts flexibility to the tubing. The outer layer is comprised of a hard plastic material which imparts structural support to the elongated hollow member (or central lumen). The combination of these two materials in a single member results in a very durable and flexible structure, exhibiting a low kink radius. Nontoxicity is achieved through the proper selection of layer materials.

Additionally, because of the low kink radius a central lumen according to the present invention has especially good resiliency characteristics. Resiliency is the restoring force which allows the central lumen to return to its original condition after, for example, a kink arises either intentionally or unintentionally during use. In the case of an IAB having a central lumen, if a kink arises, the resiliency characteristics of a central lumen according to the present invention allows the restoration to its original condition, i.e., without the kink, more quickly and more efficiently than in prior art devices.

The central lumen of the present invention is applicable to all sizes and types of double lumen IAB devices and is not limited by IAB insertion technique. It may be incorporated into IAB devices intended for insertion by the convention Seldinger technique, sheathless technique or those techniques incorporating a tear away sheath.

In addition, the catheter or central lumen of the present invention can be used in any utility where a flexible catheter or central lumen is employed, more specifically in angioplasty, as a pulmonary artery balloon catheter, for antegrade thoracic insertion, or for catheters used with pancreatic or gall bladder problems.

The elongated hollow member of the present invention can be produced by any suitable technique which is familiar to those skilled in this art. A preferred technique is a coextrusion process. In the coextrusion process, the outer layer is formed over the inner layer using an extruder suitable dies.

The inner layer in order to impart flexibility to the overall structure is made from a non-toxic material comprised of a soft elastomeric material. Such materials are well-known to those skilled in the art. Among some useful materials are polyvinyl chloride, silicone resins and polyurethanes. A preferred group of soft elastomeric plastic materials are polyurethanes. Pellethane 2363-65D, a polyether/ polytetramethylene glycol polyurethane sold by Dow Chemicals, U.S.A. is an example of a useful polyurethane.

The outer layer in order to impart structural support to the present catheter is made from a non-toxic material comprised of a hard plastic material. Such materials are well-known to those familiar with the present pertinent art area and include, polyethylene, polypropylene, polycarbonates, polysulfones, polymethylmethacrylates and nylons. A preferred group of hard plastic materials include the nylons and more preferable the hard plastic material is nylon 6.

In a preferred configuration, the catheter or central lumen of the present invention has a tubular configuration in which the inner and outer layers have constant diameters. Normally, the thickness of the outer layer is greater than the thickness of the inner layer. However, these thicknesses may be varied depending upon the application and the end result sought to be achieved. It is also possible that the diameters of the inner and outer layers may be variable either individually or together.

BRIEF DESCRIPTION OF THE DRAWING

The features of the present invention that are believed to be novel are set forth with particularity in the appended claims. The invention, together with further objects and advantages thereof, may best be understood by reference to the following description taken in conjunction with the accompanying drawings in which:

DETAIL DESCRIPTION OF THE DRAWINGS

Figure 1:
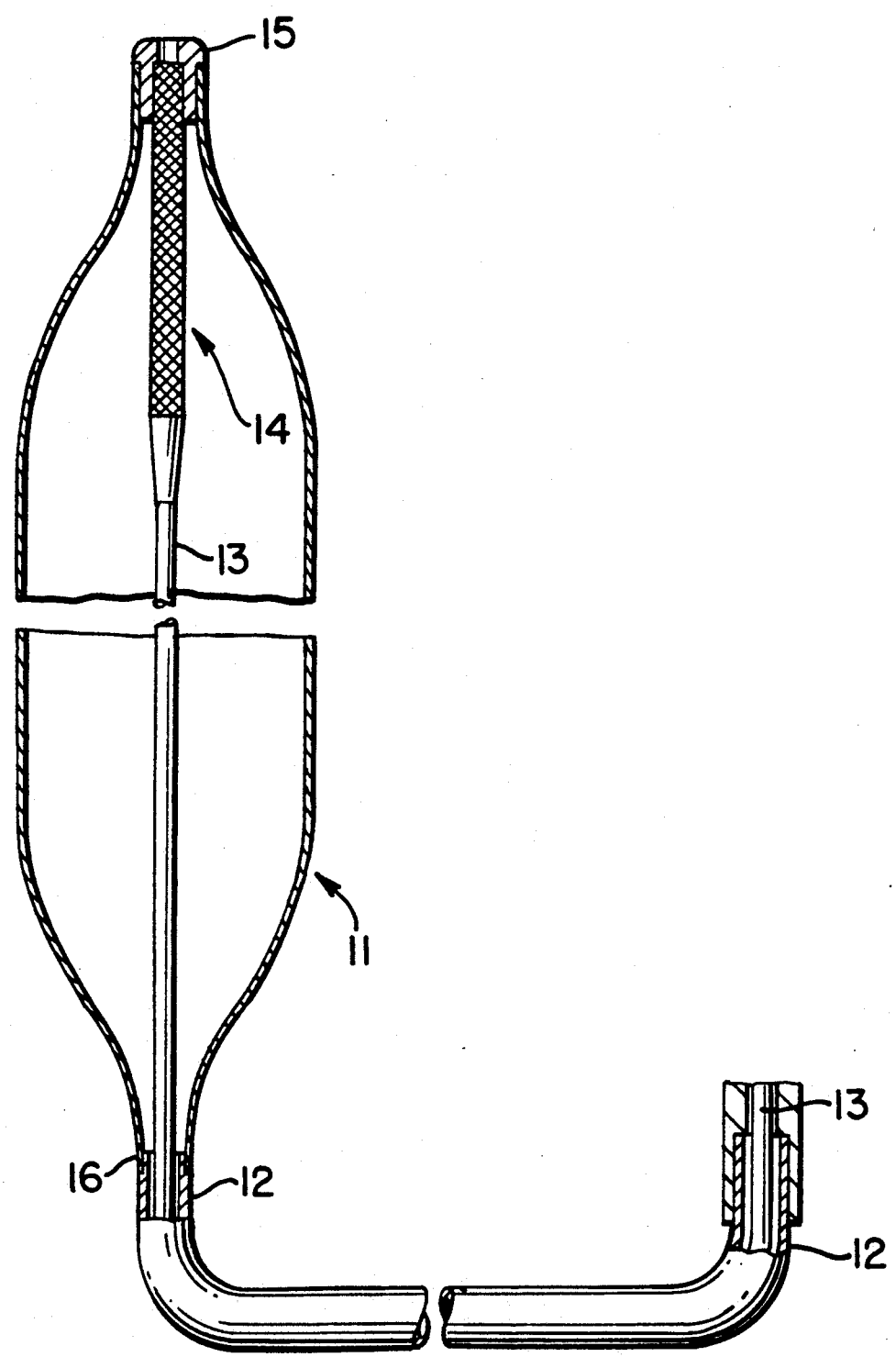
FIG. 1 is a cut-away side elevation of the partial structure of an IAB in accordance with the invention.

As shown in FIG. 1, a balloon catheter according to the invention includes a conventional single-chamber intra-aortic balloon 11 and a catheter 12 having disposed within in a elongated member or central lumen 13 which is more fully shown in FIG. 2 and FIG. 3 and described herein below. The balloon is illustrated by way of example as a conventional single chamber IAB.

The balloon 11 is preferably formed of an antithrombogenic flexible material and at is proximate end is bonded in fluid-tight manner to an end of catheter 12 and is bonded at its distal end to the flexible end 14 and elongated member or central lumen 13. Additionally, a metal ring 16 may be provided to make the balloon more easily insible to facilitate location of the balloon. Tip 15 is sealably bonded to the distal end of the balloon.

Figure 2:
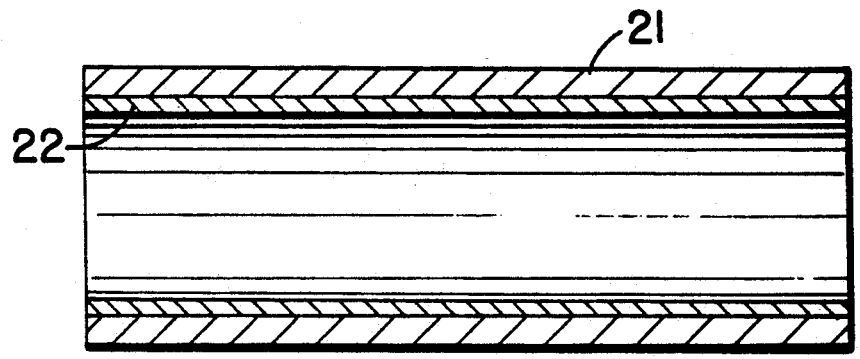
FIG. 2, is a cut-away side elevation of a tubular member according to the invention.
Figure 3:
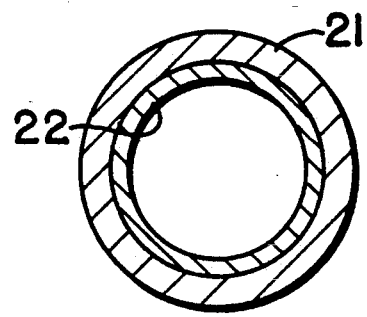
FIG. 3 is a cut-away front elevation of a tubular member according to the invention.

FIGS. 2 and 3 show side and front elevations of elongated member or central lumen 13 of FIG. 1. Inner layer 22 is comprised of a soft elastomeric plastic material onto which has been coextruded the outer layer 21. Outer layer 21 is comprised of a hard plastic material.

Although only one embodiment of the present invention has been described in detail, it should be understood that the present invention may be embodied in many other specific forms without departing from the spirit or scope of the invention.

A inner layer in tubular form of polyurethane (Pellethane 2363-65D) was prepared and a layer of nylon was formed over the polyurethane tubular layer by coextrusion. This tubular material was useful as the central lumen in an IAB device and had a kink radius which is about one third that of the central lumen of typical prior art flexible balloon catheters.

The description of the preferred embodiment of the present invention is considered to be illustrative and not restrictive and the invention is not limited to the details given herein, but may be modified within the scope of the appended claims.

We claim:

1. In a balloon catheter apparatus having a hollow catheter having a proximate end and a distal end and an inflatable and deflatable balloon having a proximate end and a distal end, the proximate end of the balloon being sealably attached to the distal end of the catheter, and an elongated member or central lumen disposed within the hollow catheter, the improvement wherein the elongated member is comprised of a dual layer comprised of an inner soft elastomeric polyurethane layer and an outer hard plastic nylon layer, the elongated member being formed by forming the outer layer onto the inner layer by coextrusion and the dual layer extends the entire length of the elongated member.

2. An apparatus according to claim 1, wherein the inner layer of the elongated member is non-toxic.

3. An apparatus according to claim 1, wherein the outer layer of the elongated member is non-toxic.

4. An apparatus according to claim 1, wherein the nylon is nylon 6.

5. An apparatus according to claim 1, wherein the elongated member exhibits good resiliency characteristics.

* * * * *